United States Patent [19]

Crosby et al.

[11] 4,014,893

[45] Mar. 29, 1977

[54] 3,4-CYCLOALKANO FUROXANS

[75] Inventors: John Crosby; Robert Allan Campbell Rennie; John Tanner, all of Runcorn, England; Robert Michael Paton, Edinburgh, Scotland

[73] Assignee: Imperial Chemical Industries Limited, London, England

[22] Filed: Aug. 5, 1975

[21] Appl. No.: 602,011

Related U.S. Application Data

[62] Division of Ser. No. 467,512, May 6, 1974, Pat. No. 3,931,106.

[30] Foreign Application Priority Data

May 11, 1973 United Kingdom ............ 22582/73
June 26, 1973 United Kingdom ............ 30218/73
Nov. 12, 1973 United Kingdom ............ 52380/73

[52] U.S. Cl. .................................. 260/307 DB
[51] Int. Cl.$^2$ .................................. C07D 271/12
[58] Field of Search ...................... 260/307 DB

[56] References Cited

UNITED STATES PATENTS 3,931,214  1/1976  Kampe et al. ............... 260/307 DB

OTHER PUBLICATIONS

Klamann et al–C.A. 69, 10442j (1968)–Abstract of German 1,257,150 of 12-28-67.
Morrison et al. "Organic Chemistry," 1966, pp. 278–280.

*Primary Examiner*—Donald G. Daus
*Assistant Examiner*—David E. Wheeler
*Attorney, Agent, or Firm*—Cushman, Darby & Cushman

[57] ABSTRACT

3,4-Cycloalkano furoxans are produced and are found to be useful in cross-linking of polymers.

2 Claims, No Drawings

3,4-CYCLOALKANO FUROXANS

This is a division, of application Ser. No. 467,512 filed May 6, 1974 which is now U.S. Pat. No. 3,931,106.

This invention relates to the formation of dinitrile oxides and their subsequent use in addition reactions.

On heating, furoxans may be made to undergo a reaction which is believed, without prejudice to the present invention, to involve cleavage of the heterocyclic furoxan ring to produce two nitrile oxide groups. Using compounds in which a monocyclic or polycyclic ring system is fused to the furoxan ring, the products are dinitrile oxides which, by virtue of their bifunctional character may in turn be caused to react with suitable substrates and thus modify their properties, for example as cross-linking agents.

Since the furoxans themselves are commonly more stable than the derived nitrile oxides, and particularly when the nitrile oxides are aliphatic, it is advantageous to mix the furoxan with the substrate to form a mixture having a reasonable shelf-life and to generate the dinitrile oxide by heating when desired to initiate the appropriate substrate modifying reaction.

Thus, according to the present invention, a process for the modification of a polyfunctional species comprises mixing the species with a furoxan containing a monocyclic or polycyclic ring system fused to the carbon atoms of the furoxan ring, and subsequently heating the mixture to a temperature at which a dinitrile oxide compound is generated in situ by thermal decomposition of the furoxan and caused to react with the said polyfunctional species.

In this context the term "dinitrile oxide compound" is used to designate a compound containing at least two nitrile oxide groups.

By "polyfunctional species" we mean a compound or mixture of compounds including two or more reactive sites capable of entering into addition reactions (including cycloaddition reactions) with nitrile oxides or their derivatives, for example the isocyanates. The polyfunctional species may comprise a polymerisable monomer or mixture of such monomers, or may itself be polymeric.

Preferably, the polyfunctional species is a polymer containing polymer chains substantially free from cross-links and containing functional groups capable of entering into 1,3-addition or 1,3-cycloaddition reactions with the nitrile oxide.

Examples of such groups include olefinic double bonds, acetylenic triple bonds, >C=N - groups, nitrile groups, carbonyl groups, hydroxyl, thiol, amino, and carboxylic acid groups.

A full discussion of 1,3-dipolar cycloadditions with nitrile oxides is contained in Chapter V of the monograph by Ch. Grundmann and P Grünanger — The nitrile Oxides, published in 1971 by Springer-Verlag (Berlin, Heidelberg and New York). Reference is directed to that work for a further discussion of the propensity of nitrile oxides to enter into 1,3-dipolar cycloadditions.

Nitrile oxides are, generally, reactive species, while furoxans may be more stable. Thus, a furoxan may be mixed with a polyfunctional species under conditions such that the system is stable. In this way, mixtures may be prepared having reasonable shelf lives. If the temperature of the mixture is then raised above the decomposition temperature of the furoxan, the corresponding nitrile oxides are generated in situ and react with the polyfunctional species.

Thus, a polymerisable monomer containing groups capable of entering into 1,3-addition or 1,3-cycloaddition reactions with nitrile oxides may be heated with a furoxan so as to form a nitrile oxide adduct. The monomer may then be polymerised to form a polymer having nitrile oxide derivatives incorporated into the polymer structure, with consequent modification of the properties of the product polymer. Depending on the nature of the polymerisable monomer and the relative proportions of the monomer and the furoxan the nitrile oxide adduct may be formed before, simultaneously with or subsequently to the polymerisation reaction.

Alternatively, the polyfunctional species may be polymeric, provided that it still contains functional groups capable of reaction with the nitrile oxide as it is formed.

On heating a mixture of such a polymeric material with a suitable furoxan, the furoxan decomposes to a dinitrile oxide which may react with two functional groups. If these functional groups are on different polymer chains a cross-link will be formed between these chains, and if a sufficient number of such cross-links are produced the properties of the polymeric material will be considerably modified. Such a process, is particularly applicable to rubbers, in which cross-linking reactions produce a 'cured' rubber of higher modulus and better operating properties then the uncured material.

The reaction of a polyfunctional species with a dinitrile oxide may also be used to produce polymeric materials. Thus, for example, a diene or a dinitrile will react with a dinitrile oxide to produce a polymer consisting of hydrocarbon residues linked by isoxazoline or oxadiazole units, respectively. The polyfunctional species may contain only one type of functional group, as indicated above, where the polyfunctional species is the diene or dinitrile. Alternatively the polyfunctional species may include more than one functional group, which may be in the same molecule, as in the olefinically unsaturated nitriles or in different molecules, as in a mixture of a diene and a dinitrile. The latter possibility permits the production of copolymers, particularly random copolymers, where the monomer units are derived from several different types of compounds.

Depending on the structure of the polyfunctional species and the furoxan from which the dinitrile oxide is generated, the polymers produced may be linear or cross-linked. Thus, for example, adiponitrile will react with a dinitrile oxide to form a linear poly(1,2,4-oxadiazole), while glycerol will form a cross-linked polyurethane. (In this case, the nitrile oxide would have had to isomerise to isocyanate prior to reacting with the hydroxyl groups). Cross-linked products may also be produced by employing starting materials which will generate nitrile oxides having a functionality greater than two, or dinitrile oxides which contain, double bonds or other unsaturation, e.g.

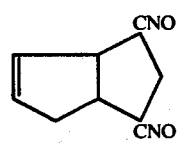

I

Reaction with a dinitrile oxide generated by thermal decomposition of an appropriate furoxan may also provide a convenient route for chemically bonding additives to a polymer.

For example, a polymer or monomer capable of acting as a polyfunctional species in our process may be heated with a mixture of a suitable furoxan and an additive including a functional group also capable of entering into addition reactions with nitrile oxides. When the dinitrile oxide is formed, one of the nitrile oxide groups may react with the said monomeric or polymeric species, and the other nitrile oxide group may react with the functional group of the additive, so that it becomes chemically bonded to the polymer structure through the nitrile oxide derivative.

Examples of additives which may be introduced into a polymer structure in this way include dyes, soil release agents, antistatic agents, antioxidants and water repellents.

When the process of our invention is applied to crosslinking, the reaction may be confined to a part only of a mass of polymeric material. Thus, for example, articles composed of an acrylonitrile-butadiene-styrene copolymer may be treated with a nitrile oxide precursor in order to cross-link the surface of the article, giving an effect analogous to case-hardening of metals. If the nitrile oxide is permitted to isomerise to isocyanate, a similar reaction may apply to materials containing surface hydroxyl groups, for example cellulosic articles or —OH terminated polyesters.

Many materials usable as reinforcements for a polymeric matrix contain functional groups reactable with nitrile oxides (or isocyanates), and these may be chemically bonded to the polymer matrix through a dinitrile oxide. Thus, for example, an unsaturated polyester may be bonded to a fibre reinforcement, using sites of unsaturation in the polyester and the fibre. If the reinforcing agents contain surface hydroxyl groups as, for example, with cellulosic fibres or glass fibres, the nitrile oxide may alternatively react as the isocyanate, forming a urethane linkage. Alternatively, hydroxylic fillers, e.g. glasses, may be treated with a vinyl silane and then bonded to the polymer matrix through the vinyl groups.

Depending on the furoxan used, the reaction with the polyfunctional species may be closely controlled. The employment of a furoxan which is stable at room temperature permits the development of polymer-forming of polymer-modifying systems having useful shelf life and ease of fabrication. Thus, for example, an unsaturated monomer or mixture of monomers, for example a diene or dinitrile, may be mixed with a furoxan to form a liquid composition which may be cast into a desired shape and then polymerised merely by the action of heat. Similarly, a rubber or an unsaturated polyester, for example, may be blended with a furoxan and, after shaping, cross-linked by heating the composition. Thus, the polymerisable mixture or curable composition, containing a predetermined quantity of furoxan may be prepared in bulk by the polymer manufacturer and stored until required. The composition may subsequently be shaped as desired, for example by moulding or casting, and cured merely by the application of heat, there being no necessity to add a polymerisation initiator or cross-linking agent at the fabrication stage. Furthermore the amount of furoxan incorporated in the mixture gives overall control of the degree of crosslinking, by virtue of the stoichometry of the reaction.

It is also possible to employ a mixture of furoxans as precursors for the nitrile oxides, the furoxans having different decompositions temperatures. Thus, a composition might be partially cross-linked by heating it to a temperature which is high enough to decompose one furoxan, but is below the decomposition temperature of the second furoxan. Cross-linking could then be completed by raising the temperature of the composition above the decomposition temperature of the second furoxan. Cross-linking by the process of our invention may also be combined with conventional crosslinking reactions, for examples, vinyl polymerisation, either consecutively or concurrently. Such two-stage curing systems enable one to produce, for example, a partially cured article, such as a sheet, which combines flexibility with reasonable mechanical strength, and which may be shaped readily and subsequently cured thermally to give a rigid article.

A wide variety of furoxans may be used in the practice of the present invention, provided that the carbon atoms of the furoxan ring are fused to a monocyclic or polycyclic ring system. This ring system may be aromatic or aliphatic or a mixture of the two, the aliphatic ring, when present, being saturated or unsaturated. Inert substituents may also be attached to the carbon atoms of the ring system or form part of the ring system.

Examples of suitable furoxans include: The 3,4-alkanofuroxans of general formula

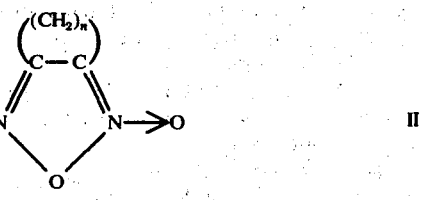

II where $n$ is an integer of at least 2, and preferably from 3 to 10. 3,4-(1', 4'-methano-2', 3'-$\Delta^2$-propeno)butano furoxan (Dicyclopentadiene furoxan)

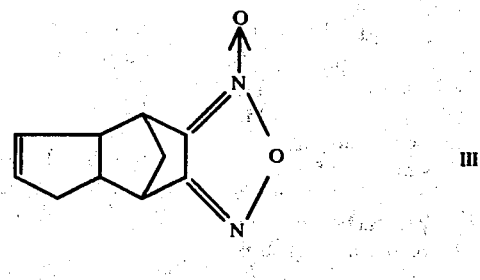

III 3,4-(1', 4'-methano)butano furoxan

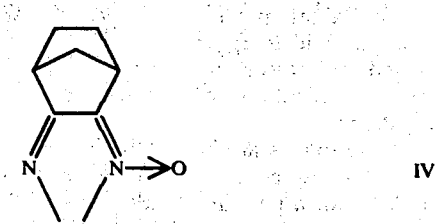

IV 3,4-(1', 4'-ethano)butano furoxan

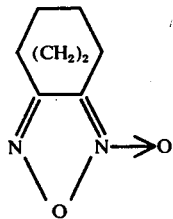

3,4-(1', 4'-methano-2', 3'-propano)butano furoxan

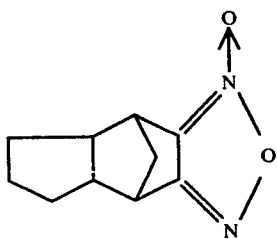

VI and acenaphthene furoxan (acenaphtho-[1,2]furazan-N-oxide)

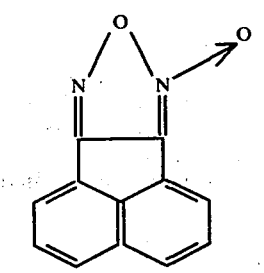

VII

Other useful nitrile oxide precursors are cyclic hydrocarbons bearing more than one furoxan ring fused to the same or different hydrocarbon rings, for example, the isomeric furoxans formally derived from norbornadiene.

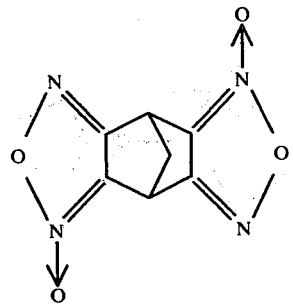

VIII which decompose to give propane-1,1,3,3-tetrakis(nitrile oxide).

Preferred furoxans, especially when the process of our invention is used for cross-linking polymeric materials, e.g. rubbers, are dicyclopentadiene furoxan (III), acenaphthene furoxan (VII) (hereinafter referred to as DCPDF and ACNF, respectively, for the sake of convenience) and 3,4-propanofuroxan.

DCPDF is a novel compound, which exists as a mixture of isomers IIIA and IIIB

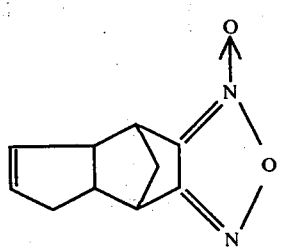

IIIA

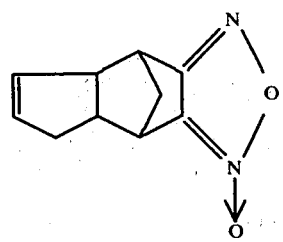

IIIB whose systematic means are 3,4-(1', 4'-methano-2', 3'-Δ$^1$-propeno)-butanofuroxan and 3,4-(1', 4'-methano-2', 3'-Δ$^2$-propeno)-butanofuroxan, respectively.

These isomers are practically identical in properties, and are both formed in the synthesis of DCPDF. Separation of the isomers is impractical and unnecessary, since the same dinitrile oxide (I) is formed by ring opening of either isomer.

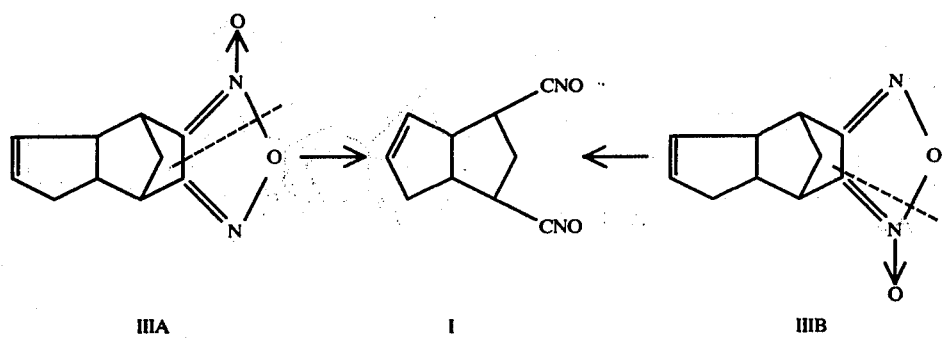

DCPDF may be produced in a three-step synthesis from dicyclopentadiene (IX), a cheap and readily available raw material. The steps of the synthesis are shown as A, B and C below, only one isomer being shown although two or more isomers are produced at each step.

higher yield than is found for other known methods of cyclodehydration.

As previously mentioned, DCPDF may find application as a cross-linking agent for unsaturated polymers and rubbers by in situ generation of the dinitrile oxide (I) which may then, for example, react with two ethyl-

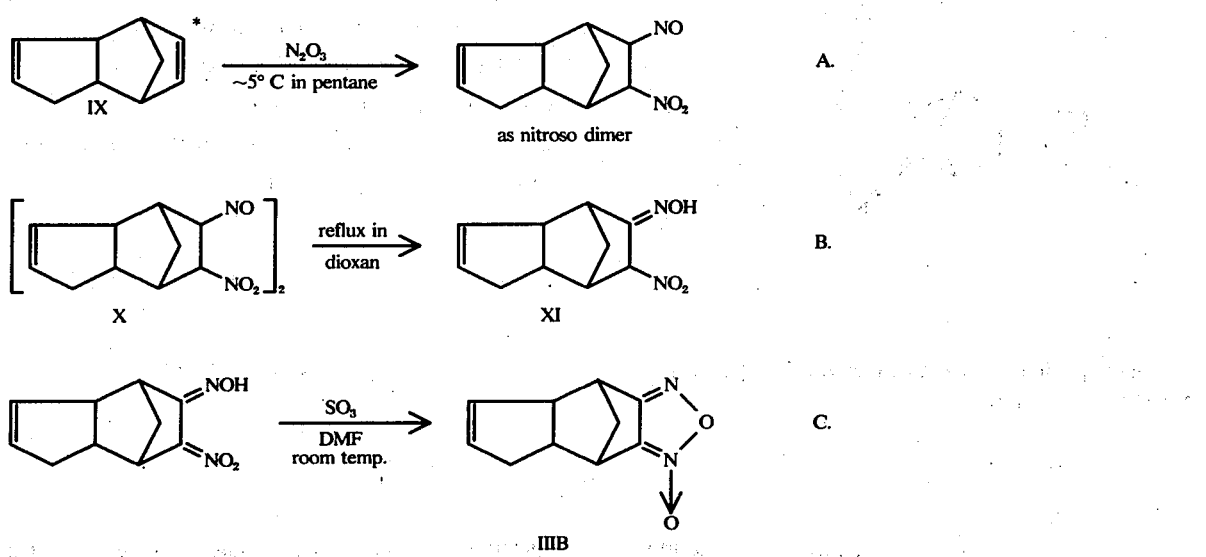

In step A, dinitrogen trioxide adds across the more reactive double bond of dicyclopentadiene, which is the one marked with a * in formula (IX) above, to give a mixture of nitrosonitro isomers, which precipitate from solution as the nitroso dimers (X). Reflux in an inert polar slvent of suitable boiling point, for example, enic double bonds or with two carbon-nitrogen triple bonds (nitrile groups). It may also be useful as an intermediate in the production of diisocyanates by thermal ring opening and rearrangement, particularly if the ethylenic double bond is first hydrogenated to give the saturated furoxan VI.

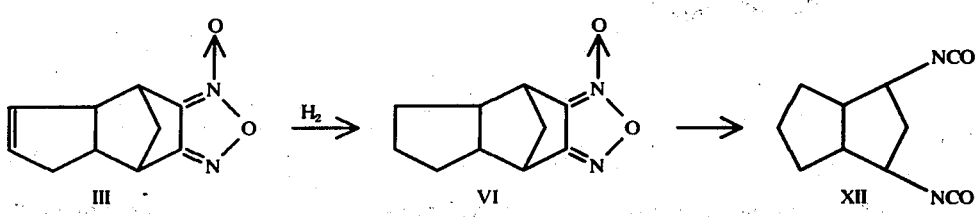

dioxan, brings about the tautomeric change from nitroso compound to oxime. Finally cyclodehydration of the nitroxime (XI) with $SO_3$ at room temperature gives the furoxan, as described in our copending British Patent Application No. 24092/73.

In the cyclodehydration reaction with $SO_3$, DCPDF may be obtained from the corresponding nitrooxime in It is believed, without prejudice to the present invention, that the temperature at which cleavage of the furoxan ring occurs, to generate nitrile oxides, is largely dependent upon the degree of strain present in the ring system fused to the carbon atoms of the furoxan ring.

Preferred furoxan cleavage temperatures are in the range 30°–280° C and especially preferred are temperatures in the range 80°–180° C. However it will be clear to those skilled in the art that particular sub-ranges of temperature may be more especially preferred for particular applications; for example 140°–170° C for the curing of bulk rubbers. Here the curing system has to be essentially stable during the compounding process but must then rapidly effect a cure when the temperature is raised to, for example 160° C. Furthermore, it will be appreciated that furoxans which cleave at temperatures only slightly above room temperature will necessarily have to be stored under refrigeration until required for use.

It will also be obvious to those skilled in the art that the ring-opening process will not, under solution conditions such as obtain when furoxans are mixed with other compatible materials, for example polymers, take place suddenly and completely at a specific temperature. For this reason the preferred temperatures are those at which the process occurs at a convenient or advantageous rate with respect to a particular application; for example, it is particularly desirable to shorten curing cycles in natural rubber processing and so a furoxan which is stable under compounding conditions but then cures in, say, 1–3 minutes, at 160° C is preferred.

It will be appreciated that the type and size of ring fused to the furoxan ring will effect the temperature of cleavage and hence the choice of furoxan for any particular application of the process of our invention. But the factors affecting this choice will be clear from the accompanying Examples, from which it will be seen that, in certain cases, furoxans which nominally cleave at temperatures which would be too high for the envisaged application may be made useful by the incorporation of suitable additives. For example, some carbon blacks may increase the rate of cleavage of a furoxan at a temperature which would otherwise be too low.

Since the ring cleavage of the furoxans does not occur instantaneously, it is possible to allow, say, curing of a rubber composition to proceed to a predetermined stage and then to cool the partially cured material below the decomposition temperature of the furoxan to arrest the cure at that stage. The material may be subsequently further cured, as desired, by raising its temperature above the said decomposition temperature.

The proportions of furoxan and polyfunctional species will vary with the nature of the components and with the type of application, e.g. whether it is intended to form a polymer from a monomer or to cross-link a polymeric material.

In the first-mentioned case the proportions will depend upon the number of nitrile oxide groups generated per molecule of furoxan and also the number of reactive groups per molecule of monomer; but in general the ratio of furoxan to monomeric material will be in the range 3:2 to 2:3, preferably 1:1.

In the second-mentioned case the proportions of furoxan to polymeric material will commonly be in the range 1:3 to 1:1000.

The process according to the invention is applicable to the curing of both natural and synthetic rubbers, or elastomers, although in the case of ACNF better results are obtained with synthetic rubbers. Without prejudice to the invention, it is considered that the close spacing between olefinic double bonds in the polymer chains of natural rubber may lead to bridging between two such bonds in the same chain rather than cross-linking between chains when reacted with the dinitrile oxide from ACNF, in which there is less separation between the nitrile oxide groups than in the case for the dinitrile oxide from DCPDF.

In the curing of rubbers by furoxans according to the invention, the rubber may be compounded with known additives, for example carbon black, certain process oils, anti-oxidants, etc. Where carbon black is present, cure times are generally shorter than in the absence of carbon black. However, additives which are used as part of conventional curing and accelerator systems, for example tetramethyl thiuram disulphide, zinc oxide and stearic acid, are unnecessary when furoxans are used as curing agents, and may even have an adverse effect upon the degree of cure.

Many types of synthetic rubbers, or elastomers, may be cross-linked by the process of our invention. Examples of such materials include the elastomeric copolymers of acrylonitrile/butadiene, styrene/butadiene, ethylene/propylene/diene, ethylene/propylene/ethylidene-norbornene, acrylonitrile/butadiene/styrene; polydienes, and the elastomeric polysiloxanes, in each case the polymer or copolymer being one which contains more than two functional groups capable of reacting with a dinitrile oxide in the polymer chain.

Examples of such groups which may be incorporated in the polysiloxanes include vinyl, allyl, methacryloxypropyl, 2-cyanoethyl, butadienyl and vinyl phenyl. Suitable polysiloxanes include poly(methyl vinyl)siloxane, poly(dimethyl) (methyl vinyl) siloxane and poly(vinyl phenyl) siloxane.

It will be appreciated that our process may also be applied to suitable latexes of such elastomers.

The curing of rubbers by furoxans according to the present invention can give rise to rapid cure times without the use of added accelerators. No gaseous by-products are produced, and the resulting cross-links may have a high degree of chemical and thermal stability. Furthermore, furoxans are generally miscible with hydrocarbon polymers allowing ease of incorporation.

In addition to rubbers, polymeric materials such as stoving coatings, for example vinylidene dichloride/acrylonitrile copolymers, may be cured via thermal decomposition of furoxans, and good solvent and corrosion resistant coatings may be obtained. A further application of furoxans as curing agents is in the curing of tung oil (a triglyceride of eleostearic acid) to give a coating suitable for the protection of machine tools, engineering parts, etc. against rust and mechanical damage.

The invention is now illustrated by the following Examples, in which quantities are expressed as parts by weight, unless otherwise stated.

EXAMPLES 1 to 3

Use of 3,4(1', 4'-methano)butano furoxan
Preparation of 3,41', 4'-methano)butano furoxan

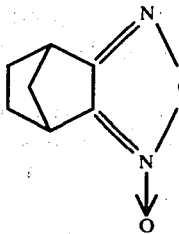

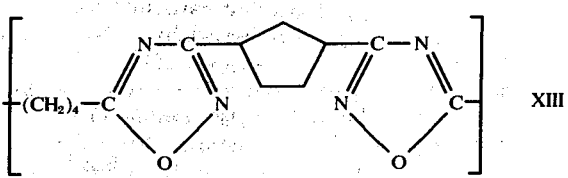

i. Norbornene pseudonitrosite was prepared by the method of Scheinbaum (J. Org. Chem., 33 (1968) 2586).

ii. Norbornene pseudonitrosite (10 g) in 1,4-dioxan (500 ml) was heated at reflux, under $N_2$, until the initial deep blue-green colour had faded to a pale yellow-green (2 hours). Solvent was removed under reduced pressure to give crude norbornene nitrooxime as an oil which slowly solidified. Addition of ether and filtration afforded pure nitrooxime (3.7 g) as colourless crystals with m.p. 155°–161° C.

Analysis: found 49.48%C; 5.89%H; 16.26%N; $C_7H_{10}N_2O_3$ requires 49.42%C; 5.92%H; 16.47%N.

iii. Benzyl chloride (4 m.moles) and the norbornene nitrooxime (4.9 m.mole) were mixed in ethanol (2 ml) and a solution of ethanolic sodium ethoxide was added (4 m.moles) of Na in 7 ml). The mixture was treated with water (2 ml) and heated at reflux under $N_2$ for 2 hours. The mixture was then evaporated to dryness, the residue dissolved in 10% aq. NaOH and extracted with $CH_2Cl_2$. The aqueous layer was separated and treated with hypochlorite solution until no further product formation was observed. The resulting emulsion was extracted with $CH_2Cl_2$ and the extracts dried and evaporated to give the furoxan.

The furoxan was characterised as follows:

It was dissolved in excess phenyl acetylene and heated at 100° C for 12 minutes; removal of the excess phenyl acetylene yielded the bis(isoxazole):

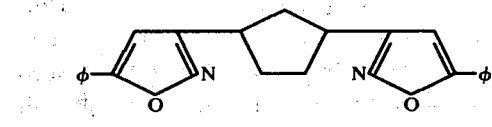

m.p. 100° C, resolidifying and remelting at 120° C.

Analysis: 75.73%C; 5.91%H; 7.97%N. $C_{23}H_{20}N_2O_2$ requires: 77.55%C; 5.62%H, 7.87%N.

EXAMPLE 1

3,4-(1',4'-methano)butanofuroxan with adiponitrile

The furoxan and adiponitrile were mixed together in a molar ratio of 1:1 at room temperature and then heated to 105° C at a rate of about 2°–3° C/min. The mixture was cooled to give a resinous material which was shown to be the polyoxadiazole formally derived by the 1,3-dipolar cycloaddition of cyclopentane-1,3-bis(nitrile oxide) and adiponitrile. The polymer repeat unit had the structure:

EXAMPLE 2

3,4(1',4'-methano)butanofuroxan with dicyclopentadiene

Dicyclopentadiene, and 3,4(1',4'-methano)-butanofuroxan, were mixed and heated as in Example 1 to give, on cooling, a brittle resinous product.

EXAMPLE 3

3,4-(1', ,4'-methano)butanofuroxan with norbornadiene dimer

The pentacyclic tetradecadiene, of structure

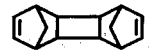

was mixed with an equimolar quantity of 3,4-(1',4'-methano)-butanofuroxan. The mixture was treated as in Example 1 to yield a brittle resinous polymer.

EXAMPLE 4

Curing a Liquid Rubber with 3,4-(1',4'-methano)butanofuroxan

A partially depolymerised natural rubber (M.Wt. $\overline{M}_n$ = c. 13500) (5 parts) and 3,4-(1',4'-methano) butanofuroxan (1 part) were dissolved in methylene chloride. The methylene chloride was removed by evaporation, to give a solution of the furoxan in the rubber. The rubber was cured by heating it from 60° C to 104° C over a period of 25 minutes.

EXAMPLE 5

Curing polybutadiene with 3,4-(1',4'-methano)butanofuroxan

A hydroxyl-ended polybutadiene (molecular weight $\overline{M}_n$ = c. 3200) (8 parts) and 3,4-(1',4'-methano)-butano furoxan (1 part) were dissolved in methylene chloride (80 parts). The methylene chloride was removed by evaporation, to give a clear solution of the furoxan in polybutadiene. This was cured to a tacky, rubbery material by heating from 80° C to 110° C over a period of 15 minutes.

EXAMPLES 6 to 43

Use of DCPDF as cross-linking agent

Preparation of Dicyclopentadiene furoxan (DCPDF)

Step A Synthesis of dicyclopentadiene pseudonitrosite (X)

A well stirred solution of dicyclopentadiene (66 g.) in n-pentane (1 l.), cooled in an ice bath, was treated with a mixed stream of nitric oxide (150 ml/min.) and air (75–100 ml/min) for 3 hours. The mixture was purged with nitrogen and the solid product filtered off, sucked dry, washed with hot methanol and dried to give an almost colourless crystalline material, wt. 69 g.

(66%) m.p. 122°–140° C, infra-red spectrum (Nujol mull) strong band at 1555 cm$^{-1}$.

Step B Synthesis of nitro oxime (XI)

The nitroso dimer from the previous preparation (20 g.) was heated at reflux under nitrogen in dioxan (500 ml.) until the initial green colouration disappeared (40 minutes). Removal of the solvent afforded a yellow oil which slowly crystallised. Washing with methanol gave 7.5 g. of clean crystalline material with m.p. 135°–150° C.

Step C Synthesis of dicyclopentadiene furoxan (III) A/B

The nitro oxime from the previous preparation (2.20 g.) and 2.3 g. of a standardised DMF-SO$_3$ mixture (containing 5% excess SO$_3$ over the stoichiometric amount required for the dehydration reaction) were mixed; a further 1.5 ml. of DMF was added to ensure the mixture was completely liquid at room temperature. The mixture was then set aside at room temperature in a stoppered flask for 65 hours.

The mixture was poured into water (60 ml.) and extracted with dichloromethane (2 × 30 ml.) to remove DMF. The acidic aqueous layer was then treated with 1N aq. NaOH until the pH was approx. 8.5. The resulting emulsion of furoxan was extracted with CH$_2$Cl$_2$ (3 × 20 ml.); the extracts were dried and evaporated to give crude furoxan as a pale yellow oil which crystallised on standing to give the crude product (2.05 g.).

Crystallisation from ether-heptane afforded the pure furoxan as pale yellow crystals:
  Yield 1.31 g. = 62%
  m.p. 98° – 100° C
  I.R. 1655 cm$^{-1}$ (v. strong) characteristic of furoxans
  C$_{10}$H$_{10}$N$_2$O$_2$ requires: 63.1%C, 5.26%H, 14.7%N
  found: 63.1%C, 5.67%H, 14.6% N.
NB DCPDF may be handled safely in solution. However, when heated to 80°–85° C on a gram scale, the solid decomposes explosively.

Characterisation of dicyclopentadiene furoxan as its bisphenylacetylene adduct (C$_{26}$H$_{22}$N$_2$O$_2$)

Dicyclopentadiene furoxan from the previous preparation (212 mg) in phenylacetylene (5 g.) was heated at 100° C for 30 minutes. Excess phenylacetylene was removed by evaporation under reduced pressure and the residual yellow solid washed with methanol, filtered, and sucked dry to give the adduct as very pale yellow crystals:
  Yield 347 mg = 79%
  m.p. 229° – 230° C
  C$_{26}$H$_{22}$N$_2$O$_2$ requires: 79.2%C; 5.59%H; 7.1 %N
  found: 78.9%C; 5.67%H; 7.1%N.

General Procedure for Cross-linking Rubbers

In the preparation of solid rubber compositions, all components other than the furoxan were milled together on conventional rubber mixing equipment, allowed to cool to room temperature then mixed with the furoxan, also on the rubber mill, for no longer than 5 minutes at a temperature not greater than 45° C.

Cure times (where given) were determined using a Wallace Shawbury cure-meter, taking the time required for the curing process as measured on the cure-meter trace to be 95% complete.

EXAMPLES 6 to 8

Use of DCPDF as cross-linking agent for natural rubbers

EXAMPLE 6

A blend of pale crepe rubber (100 parts), HAF carbon black N330 (45 parts), aromatic process oil (3.5 parts) and DCPDF (6 parts) was cured at 120° C for a total time of 10 minutes. The product was a highly cross-linked rubber with 9% compression set after 24 hours at 70° C, a hardness of 62 (BS°) and a resilience of 67% at room temperature.

EXAMPLE 7

Pale crepe rubber (100 parts) and DCPDF (3 parts) in the absence of carbon black had a cure time of 20 minutes at 102° C.

EXAMPLE 8

Pale crepe rubber (100 parts), HAF carbon black N330 (50 parts) and DCPDF (4 parts) had a cure time of <15 minutes at 102° C and <1 minute at 180° C.

EXAMPLES 9 – 17

Use of DCPDF as cross-linking agent for synthetic rubbers

Blends used, cure times and temperatures are shown in Table I.

TABLE I

| Example No. | COMPOSITION (parts by weight) | | | | | | | | cure temp. (° C) | cure time (mins) |
| --- | --- | --- | --- | --- | --- | --- | --- | --- | --- | --- |
| | SBR | NBR | AN/BA | NR | BR | EPDM | carbon black | DCPDF | | |
| 9  | 60  |     |     |     |     |     |     | 1.2 | 102 | <6  |
| 10 | 60  |     |     |     |     |     |     | 1.2 | 90  | <10 |
| 11 | 60  |     |     |     |     |     |     | 1.2 | 80  | 20  |
| 12 |     |     |     |     |     | 100 |     | 3   | 102 | 40  |
| 13 |     | 100 |     |     |     |     |     | 3   | 102 | <6  |
| 14 |     |     | 100 |     |     |     | 50  | 6   | 120 | <4  |
| 15 |     |     |     | 100 |     | 100 | 100 | 12  | 120 | 6   |
| 16 | 100 | 100 |     |     |     |     | 100 | 12  | 120 | <2  |
| 17 |     |     |     |     | 100 |     | 50  | 6   | 120 | 10  |

SBR — styrene/butadiene rubber, "Solprene 1204"
NBR — nitrile/butadiene rubber, "butakon A 3052"
AN/BA — acrylonitrile/butyl acrylate copolymer (approx 60% wt butyl acrylate)
NR — pale crepe natural rubber
BR — butyl rubber "Polysar 301"
EPDM — ethylene/propylene/diene monomer rubber "Intolan 155" cont. ENB

EXAMPLES 18 to 25

Use of DCPDF as cross-linking agent for various EPDM rubbers 6 parts of DCPDF was blended with 100 parts of EPDM rubbers incorporating a variety of termonomers, both with and without 50 parts of carbon black. Measured cure times at 120° C are shown in Table II.

TABLE II

| Example No. | EPDM | termonomer | carbon black present | approx cure time (mins) |
|---|---|---|---|---|
| 18 | "Keltan 520" | dicyclopentadiene | no | 30 |
| 19 | " | " | yes | 10 |
| 20 | "Nordel 1070" | 1,4-hexadiene | no | 20 |
| 21 | " | " | yes | 10 |
| 22 | | propylidenenorbornene | no | 30 |
| 23 | | " | yes | 10 |
| 24 | "Intolan 155" | ethylidenenorbornene | no | 30 |
| 25 | " | " | yes | 10 |

EXAMPLES 26 to 31

Effect of temperature upon cure time of EPDM/DCPDF blends

"Intolan" EPDM containing approx 10% wt ENB as termonomer (100 parts) was blended with carbon black (50 parts) and DCPDF (6 parts). The blend was cured at various temperatures and the cure time was measured as above. Tensile tests were carried out on the cured rubber and the tensile strength and elongation to break were measured. Results are shown in Table III.

TABLE III

| Example No. | Temp ° C | Cure Time (min) | Elongation to Break (%) | Tensile Strength (Kg/cm²) |
|---|---|---|---|---|
| 26 | 90 | 70 | — | — |
| 27 | 100 | 35 | 285 | 162 |
| 28 | 120 | 10 | 285 | 145 |
| 29 | 140 | 5 | 320 | 147 |
| 30 | 160 | <2 | 335 | 134 |
| 31 | 180 | <2 | 340 | 124 |

The decrease in the degree of cure with increase in temperature observed in this series of experiments is not considered to be significant. These results indicate that the reaction of the initially formed dinitrile oxide with the olefinic bonds of the rubber is probably much faster than its isomerisation to the diisocyanate even at the higher temperatures in this range. Any diisocyanate formed would probably not react with the rubber and so would contribute nothing to the curing process.

EXAMPLE 32

1.5 Weight % of DCPDF was added to a 50 weight % solution of polynorbornenyl acetate (M.Wt. ~40,000) in toluene. The resulting solution was spread on a metal plate, the solvent evaporated and the residual film of resin cured in an oven for 15 minutes at 170° C. The cured film so produced had good flexural properties and was solvent resistant.

EXAMPLES 33 to 36

Use of DCPDF to cure stoving finishes

A copolymer of 15% wt acrylonitrile and 85% wt vinylidene dichloride ("Viclan 85/02", RTM, Imperial Chemical Industries Ltd) was dissolved in tetrahydrofuran (THF). DCPDF was added to the solution, which was then painted on to substrates including metal, wood and polyethylene terephthalate film. In some cases titanium dioxide pigment was ball milled into the solution before painting.

The THF was removed by evaporation and the resulting film cured at 105° C for 15 minutes. The cured film was tested for solvent resistance by immersing in THF, then in dimethyl formamide (DMF), and scrubbing the surface. Good solvent resistance is indicated by no loss of surface gloss. Results are shown in Table IV.

TABLE IV

| Example No. | COMPOSITION (parts by weight) | | | | Effect of THF/DMF treatment |
|---|---|---|---|---|---|
| | "Viclan 85/02" | THF | TiO₂ | DCPDF | |
| 33 | 5 | 45 | — | 1.35 | no loss of gloss |
| 34 | 5 | 45 | — | 0.68 | no loss of gloss |
| 35 | 5 | 45 | — | 0.34 | some loss of gloss but better than control |
| 36 | 5 | 45 | 5 | 0.68 | no loss of gloss |
| Control | 5 | 45 | — | — | finish removed |

EXAMPLES 37 to 39

Use of DCPDF to cure Tung Oil

Mixtures of tung oil and a solution of DCPDF in methylene chloride were painted on a metal substrate, and the methylene chloride removed by evaporation. The film of oil was then cured at 105° C for 15 minutes, with the results shown in Table V.

TABLE V

| Example No. | COMPOSITION (parts by weight) | | | appearance of cured film |
|---|---|---|---|---|
| | tung oil | DCPDF | methylene chloride | |
| Control | 10 | — | — | white, thin solid layer covering uncured oil |
| 37 | 9 | 1 | 4 | yellow, tacky, rubbery |

TABLE V-continued

| Example No. | COMPOSITION (parts by weight) | | | appearance of cured film |
|---|---|---|---|---|
| | tung oil | DCPDF | methylene chloride | |
| 38 | 8 | 2 | 8 | yellow, dry, flexible |
| 39 | 7 | 3 | 12 | yellow, tack-free, strong |

A film prepared as in Example 38 was used to coat a chisel blade, giving a tough coating protecting the cutting edge.

EXAMPLE 40

Curing a liquid polybutadiene

A mixture of dicyclopentadiene furoxan (1.5 parts by wt.) and a liquid polybutadiene (m.wt. 3200–3500) (20 parts by wt.) was vacuum degassed and then cured at 95° C for 20 minutes to give a clear, almost colourless, slightly tacky rubber.

It will be appreciated that the above system comprises a "one-shot" casting system.

EXAMPLES 41 and 42

Cross-linking Polysiloxanes

EXAMPLE 41

Portions of a poly(methyl vinyl)siloxane, M.Wt $\simeq 2 \times 10^5$ and containing 13 mole % of vinyl groups, were mixed with various amounts of a THF solution of DCPDF, to give concentrations of DCPDF in the mixture of 25, 10, 5, 2.5 and 1% by weight respectively. The solvent was evaporated in each case and the resultant material cured at 100° C for 10 minutes. The materials cured to give an elastomeric product in each case, the products being softer as the concentration of DCPDF decreased. A control experiment with no DCPDF resulted in the siloxane remaining uncured.

The experiments were repeated with a cure time of 5 minutes and identical results obtained.

The experiment with 5% DCPDF was repeated with 4, 3 and 2 minute cures at 100° C, and with 3, 2 and 1 minute cures at 120° C. In each case the cured materials appeared to be identical.

EXAMPLE 42

A 50:50 wt:wt mixture was prepared of a low mol. wt. liquid poly(dimethyl)siloxane (F111/50) and a poly(-dimethyl) (methyl vinyl) siloxane (EP 6295) containing 2 mole % of vinyl groups. The mixture was added to a tetrahydrofuran solution of DCPDF and the solvent removed at room temperature. Mixtures containing different amounts of DCPDF were then cured for 5 minutes at 100° C. Results are given in Table VI.

TABLE VI

| DCPDF (Wt %) | Nature of Product |
|---|---|
| 10 | opaque "cheesy" product |
| 5 | opaque "cheesy" product |
| 2 | transparent gel |
| 1 | transparent gel |
| 0.5 | transparent gel |
| 0.25 | slightly tacky transparent gel |

EXAMPLE 43

Cross-linking a Polyether

A vinyl ended polyether of formula

and DCPDF were dissolved in chloroform in the mole ratios 1:1.2 and 1:1 respectively. The $CHCl_3$ was removed under vacuum at 40° C (the polyether melts at 35°–40° C). The mobile solution was cured at 100° C for 5 minutes giving a viscous sticky fluid in the latter case. However, when 1.2 mole of DCPDF was employed, the mobile liquid cured to quite a tough elastomer, showing that this would form a useful casting system.

EXAMPLES 44 to 49

Cross-linking with ACNF

Preparation of Acenaphthene Furoxan (ACNF)

A solution of hydroxylamine was prepared by mixing concentrated aqueous solutions of hydroxylamine hydrochloride (35.1 g) and sodium acetate trihydrate (68.7 g), and added to 1 liter of industrial methylated spirits. Acenaphthoquinone (XIV) (45.5 g.) was added with stirring, and the mixture stirred under reflux for 5½ hours then evaporated to dryness. The resulting crude acenaphthoquinone dioxime (XV) was dissolved in the minimum quantity of 5% aqueous sodium hydroxide, and the solution was filtered. The filtrate was treated with alkaline hypochlorite solution until no more precipitate was obtained. The precipitate was collected by filtration, washed with water and dried in air. The crude furoxan (VII) thus obtained was recrystallised from methylene chloride using a Sohxlet apparatus to give crystalline acenaphthene furoxan, m.p. 163°–167° C. (depending on rate of heating). Yield 24 g. = 46%.

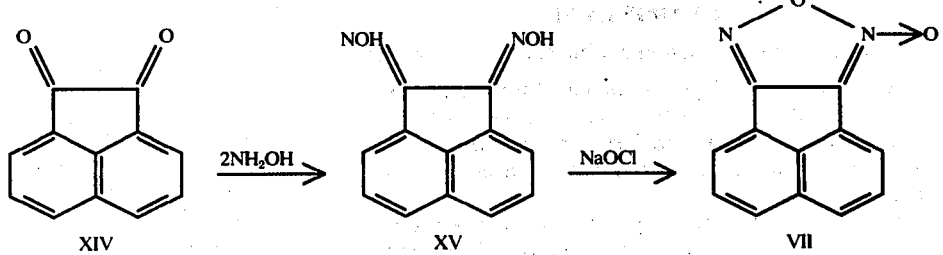

Use of ACNF as a cross-linking agent for synthetic rubbers 100 parts of rubber and 50 parts of HAF carbon black (ASTM class N330) were blended together and mixed with 6 parts ACNF as described above. The resulting mixtures were cured at 150° C, giving cure times as shown in Table VII. Cure times in the absence of carbon black were longer by factors of from 3 to 5.

TABLE VII

| Example No. | Rubber | Cure Time (mins.) |
|---|---|---|
| 44 | Nitrile/butadiene (NBR) - "Butakon A 3052" | 5 |
| 45 | Styrene/butadiene (SBR) - "Solprene 1204" | 1 |
|  | Ethylene/propylene/ethylidene-norbornene (EPDM/ENB) - "Intolan" |  |
| 46 | containing 10% wt ENB | 5 |
| 47 | containing 6% wt ENB | 5 |
| 48 | containing 3% wt ENB | 5 |
| 49 | Neoprene (WRT) | 20 |

EXAMPLE 50

Urethane from 3,4-Decanofuroxan

A solution of 3,4-decanofuroxan (10 parts) in n-decanol (60 parts) was heated under reflux for 1 hour. On cooling, a white solid was formed, which, after separation by filtration and recrystallisation from ethanol, was shown to be the bis-carbamate derived from decamethylene diisocyanate and n-decanol according to the following equation:

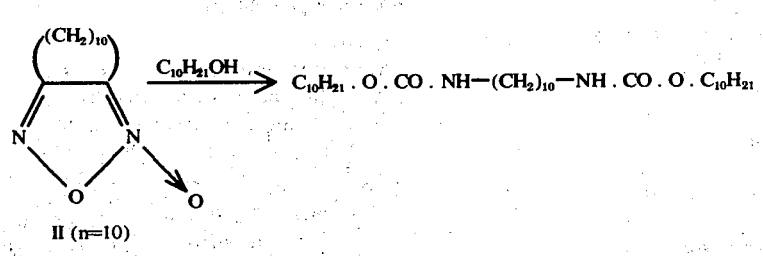

II (n=10)

The product was isolated in 70% yield and was identified by infra-red, nuclear magnetic resonance and mass spectral techniques.

EXAMPLES 51

Cross-linking polybutadiene with 3,4-decanofuroxan

A hydroxyl-ended polybutadiene (molecular weight $\overline{M}_n = 3200$) (5 parts) was mixed with 3,4-decanofuroxan (1 part) to form a homogeneous liquid. This was heated at 250° C for 15 minutes to give a rubber.

A sample of the furoxan-polybutadiene mixture used in Example 5 was unchanged after storage in an airtight can for 6 months. On heating to 250° C for 15 minutes the mixture cured to give a rubber. This illustrates the shelf-life of such mixtures.

EXAMPLE 52

Curing Nautral Rubber using 3,4-Propanofuroxan
Preparation of 3,4-Propanofuroxan

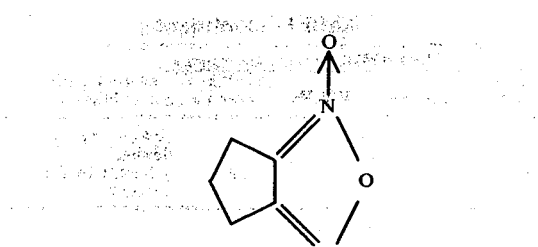

A. via the dioxime

Cyclopentane-1,2-dione (prepared by the method of Acheson, *J. Chem. Soc.* (1956) 4236) (6.66 g.) was added to a solution of $NaOAc.3H_2O$ (18.5 g.) and $NH_2OH.HCl$ (9.45 g.) in IMS (200 ml.) containing approx. 5% v/v water. The mixture was heated at reflux for 1 hour, evaporated to dryness, dissolved in 1N aqueous NaOH and treated with an excess of alkaline hypochlorite solution. The total volume was made up to 300 ml. with water and the solution extracted with dichloromethane. The extracts were dried and evaporated to give an almost pure sample of the furoxan as a mobile oil (m.p. 20° C); infra red 1670 $cm^{-1}$ (strong, furoxan);

Analysis: Found: 44.24%C; 4.74%H, 21.02%N Required: 47.5%C; 4.80%H; 22.2%N.

B. via the nitrooxime i. Cyclopentene (50 g.) in pentane (400 ml.) was treated at 5° C with a mixed stream of nitric oxide (225 cc/min) and air 100 cc/min). The precipitate of pseudonitrosite was filtered off and washed with ether to afford a colourless cyrstalline solid, m.p. 88°–90° C;

Analysis: Found: C 41.3%; H 6.03%; N 18.3%; $C_5H_8N_2O_3$ Required: C 41.6%; H 5.56%; N 19.4%.

ii. The cyclopentene pseudonitrosite (21 g) was heated at reflux under $N_2$ for 1 hour in 1,4-dioxan (200 ml); the dioxan was removed under reduced pressure to give the crude nitrooxime.

iii. $DMF/SO_3$ (containing 5% XS over the stoichiometric amount of $SO_3$ required) was slowly added to a stirred solution of the crude nitrooxime (10 g.) in DMF (10 ml.) The mixture was set aside at room temperature for 1 hour and then poured into water (200 ml) and adjusted to pH 10 with aqueous NaOH solution. The aqueous solution was extracted with $CH_2Cl_2$ and evaporated. The residue was taken up in pentane and washed with water. The pentane solution was dried and evaporated to afford furoxan identical with that prepared by method (A).

The furoxan products obtained by procedures (A) and (B) were found to give identical NMR analyses, which were as follows:

NMR ($CDCl_3$): 7.10, (triplet)

In the ratio

| -continued | |
|---|---|
| 7.22, (split triplet) | 1.0:1.0:1.0 |
| 7.38, (multiplet) | |

Characterisation as the bis benzonitrile adduct of propane 1,3-dinitrile oxide The furoxan (0.5 g.) in benzonitrile (20 g.) under $N_2$ was heated rapidly to reflux, reflux temperature was maintained for 5 minutes and the mixture allowed to cool. Excess benzonitrile was removed under reduced pressure and the crude product recrystallized from methanol of give the bis oxadiazole ($C_{19}H_{16}N_4O_2$)

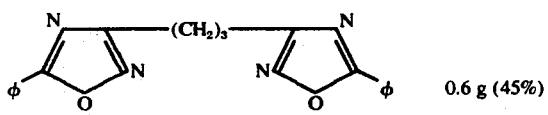

0.6 g (45%)

m.p. 97°–99° C.
Analysis: Required: 68.6%C; 4.82%H; 16.9%N. Found (i) 67.7%C; 4.81%H; 16.2%N. (ii) 70.6%C; 5.35%H; 16.7%N.

Curing Procedure

Pale crepe natural rubber (20 parts) and HAF carbon black (10 parts) were mixed in an internal mixer at 60° C for 6 minutes, 3,4-propanofuroxan (1.5 parts) was then added and mixing continued for a further 2 minutes. Samples of the resulting furoxan-containing rubber were cured at various temperatures on a Wallace-Shawbury Curometer; the following results were obtained:

| Cure temp. | 88° C | 102° C | 120° C | 130° C |
|---|---|---|---|---|

| -continued | | | | |
|---|---|---|---|---|
| Cure time: | >2 hrs; | ~1.5 hr; | >0.5 hr; | ~12 mins. |

EXAMPLE 53

Chain Extension
Preparation of Elastomer from poly(tetrahydrofuran)

Vinyl end groups are attached to poly (THF) via reaction of the toluenediisocyanate/hydroxyethylmethacrylate adduct (XIV) with poly THF of 2020 $\overline{M}_n$, as illustrated below.

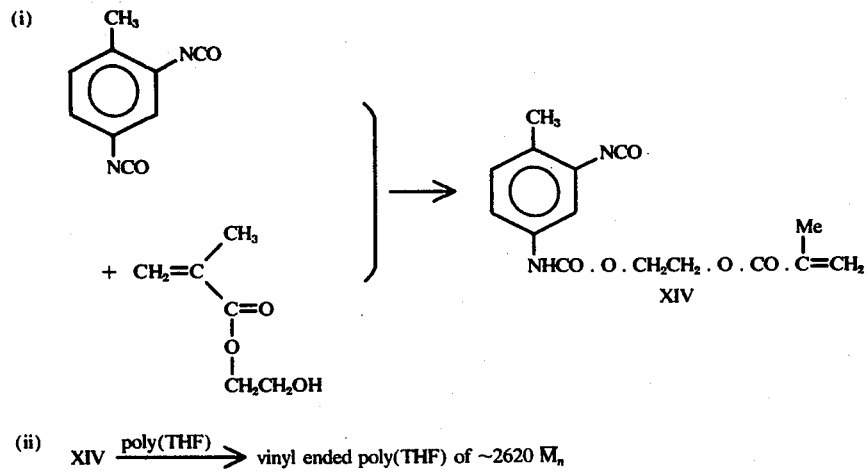

(ii) XIV $\xrightarrow{\text{poly(THF)}}$ vinyl ended poly(THF) of ~2620 $\overline{M}_n$

Chain Extension Procedure

Vinyl ended poly(THF) (26 g.) and DCPDF (2.38 g.) (i.e. in 4:5 molar ratio) were mixed in chloroform. The solvent was removed at 40° C and the polymer cast as a sheet at 40° C and cured at 100° C for 1 hour. The resulting chain extended polymer had tensile strength at break of 105 Kgs $cm^{-2}$, elongation to break 600%, 100% modulus 10.5 Kg $cm^{-2}$.

EXAMPLE 54

Cross-linking and Chain extension

Vinyl ended poly(THF) (31 g.), triallylcyanurate (0.41 g) and DCPDF (4.15 g.) (i.e. 6:1 ratio of poly(THF) to TAC and a 50% excess of DCPDF) were mixed together. The mixture was blended using solutions in diethyl ether which was then removed under reduced pressure. The product was then cast as a sheet and cured at 100° C for 2 hours to give an elastomer with tensile strength at break of 148 Kg $cm^{-2}$, elongation at break 190%, 100% modulus 50 Kg $cm^{-2}$.

It should be noted that although the Examples relate only to the curing of single rubber compositions, the process of our invention may also be applied to rubber blends.

What we claim is:
1. 3,4-(1',4'-methano-2,3'-$\Delta^2$-propeno)butano furoxan.
2. 3,4-(1',4'-methano)butano furoxan.

* * * * *